US006204050B1

(12) United States Patent
Dicosimo et al.

(10) Patent No.: US 6,204,050 B1
(45) Date of Patent: Mar. 20, 2001

(54) **PRODUCING DIASTEREOMERS OF 4-HYDROXYPROLINE USING 4-HP EPIMERASE FROM *SERRATIA MARCESCENS* OR *ACINETOBACTER BAUMANNI***

(75) Inventors: Robert Dicosimo, Rockland, DE (US); Susan K. Fager, Northeast, MD (US); John E. Gavagan, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/356,838

(22) Filed: Jul. 19, 1999

Related U.S. Application Data

(60) Provisional application No. 60/095,516, filed on Aug. 6, 1998.

(51) Int. Cl.[7] .............................. C12P 41/00; C12P 13/24
(52) U.S. Cl. ........................................... 435/280; 435/107
(58) Field of Search ........................................ 435/280, 107

(56) References Cited

U.S. PATENT DOCUMENTS 3,860,607   1/1975   Leonardo et al. ................. 260/326.2

FOREIGN PATENT DOCUMENTS 60-221083   5/1985   (JP) .

OTHER PUBLICATIONS

Enzyme Nomenclature, 1992, Academic Press Inc., p 494–495.

Greenstein, J. P. et al., Chemistry of the Amino Acids, John Wiley and Sons; New York, vol.3, chapter 29, 1961 p. 2019–42.

Adams et al., *J. Biol. Chem*, 239, 1525–1535, 1964.

Finlay et al., *J. Biol. Chem*, 245, 5248–5260, 1970.

Ito et al., *Anal. Biochem.*, 151, 510–514, 1985.

Monoharan et al., *J. Biosci.*, 2, 107–120, 1980.

Drawert et al., *Chem. Mikrobiol.*, Technol. Lebensm. 5, 165–169, 1978 (German with English abstract).

Jayaraman et al., *Indian J. Biochem.*, 2, 153, 1965.

Adams et al., *Methods Enzymol.* 17B, 266–306, 1971.

*Primary Examiner*—Sandra E. Saucier

(57) ABSTRACT

The present invention relates to two novel microorganisms, *Acinetobacter baumanni* WT-50/50-4A (ATCC 202144) and *Serratia marcescens* WT-L-4A1(RED) (ATCC 202145) characterized by 4-hydroxyproline epimerase activity. The compounds trans-4-hydroxy-L-proline (THLP) or cis-4-hydroxy-D-proline (CHDP) are converted with this epimerase activity to a mixture of THLP and CHDP. Additionally, the compounds trans-4-hydroxy-D-proline (THDP) or cis-4-hydroxy-L-proline (CHLP) are converted with this epimerase activity to a mixture of THDP and CHLP.

6 Claims, No Drawings

PRODUCING DIASTEREOMERS OF 4-HYDROXYPROLINE USING 4-HP EPIMERASE FROM *SERRATIA MARCESCENS* OR *ACINETOBACTER BAUMANNI*

This application claims benefit of Provisional Application No. 60/095,516, filed Aug. 6, 1998.

FIELD OF THE INVENTION

This invention is in the field of biocatalysis. More specifically, this invention pertains to the discovery of novel 4-hydroxyproline epimerases and to their use to convert either trans-4-hydroxy-L-proline or cis-4-hydroxy-D-proline to a mixture of trans-4-hydroxy-L-proline and cis-4-hydroxy-D-proline.

BACKGROUND OF THE INVENTION

The agricultural and pharmaceutical industry seeks production of compounds in high yield, and when a compound contains one or more chiral centers, it is often desirable to produce a single isomer. The products of the present invention are useful as precursors for chemicals of high value in these industries. Specifically, cis-4-hydroxy-D-proline (CHDP) and trans-4-hydroxy-L-proline (THLP) are useful for preparing agrochemicals and pharmaceuticals.

CHDP is prepared commercially by the chemical epimerization of THLP (Greenstein, J. P. and Winitz, M., *Chemistry of the Amino Acids,* vol.3, chapter 29, John Wiley and Sons: New York (1961)). Required for the synthesis of CHDP, THLP is prepared commercially from hydrolyzed animal gelatin, which contains approximately 13% of the desired amino acid (U.S. Pat. No. 3,860,607). Chemically epimerizing THLP to CHDP uses either basic reaction conditions (e.g., barium hydroxide under pressure at 200° C. for 6 h) or acidic reaction conditions (e.g., refluxing acetic acid/acetic anhydride). Producing mixtures of THLP and CHDP by chemical epimerization typically (1) uses high temperatures, (2) requires separating the base or acid from the desired hydroxyproline diastereomers before separating CHDP from THLP, and (3) produces highly caustic or acidic waste streams. These conditions introduce undesirable cost and handling risks.

Enzymes, as opposed to harsh chemicals, can also be used in epimerization reactions. Reactions carried out with the aid of enzymes or intact microorganisms have been used with increasing frequency and increasing success to catalyze synthetic chemical reactions. Biological processes are commonly perceived as being less harmful to the environment than chemical manufacturing processes. Amino acid racemases catalyze formation of a racemic mixture from either the D or L form of the free amino acid by equilibrating configuration at the α-carbon. Amino acid epimerases also catalyze equilibration of configuration at the α-carbon. However, since epimerases act on compounds possessing an additional asymmetric carbon, a diastereomer of the substrate is formed rather than its antipode.

4-Hydroxyproline epimerase (EC 5.1.1.8, also known as hydroxyproline 2-epimerase) catalyzes the conversion of THLP to CHDP and CHDP to THLP. The enzyme was the first amino acid-racemizing enzyme to be characterized in an essentially homogenous state, permitting direct investigation of cofactor status (Adams et al., *J. Biol. Chem.* 239:1525–1535 (1964)). An approximately equimolar mixture of THLP and CHDP is obtained when starting with either diastereomer. The enzyme also epimerizes cis-4-hydroxy-L-proline (CHLP) or trans-4-hydroxy-D-proline (THDP) to a mixture of CHLP and THDP. 3-Hydroxyprolines have also been reported to be substrates for the enzyme.

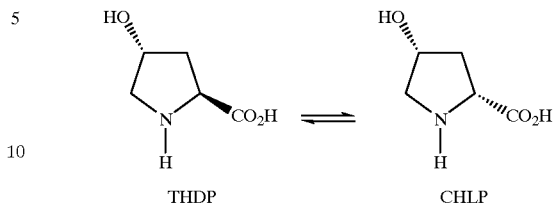

THDP CHLP

4-Hydroxyproline epimerase has been isolated from *Pseudomonas putida* (Finlay et al., *J. Biol. Chem.* 245:5248–5260 (1970)), *Pseudomonas striata* (Adams et al., *J. Biol. Chem.* 239:1525–1535 (1964)), *Pseudomonas fluorescence* (Ito et al., *Anal. Biochem.* 151:510–514 (1985)), *Pseudomonas aeruginosa* (Manoharan et al., *J. Biosci.* 2:107–120 (1980)), *Pseudomonas ovalis* and Alcaligenes sp. (Drawert et al., *Chem., Mikrobiol., Technol. Lebensm.* 5:165–169 (1978)), Achromobacter (Jayaraman et al., *Indian J Biochem.* 2:153 (1965)), and *Aerobacter aerogenes* (Adams et al., *Methods Enzymol.* 17B:266–306 (1971)). In addition, the enzyme has been isolated from a fermentation of Pseudomonas No. 109 which was cultured in the presence of 4-hydroxy-L-proline (JP 60221083).

Although these sources of 4-hydroxyproline epimerase are known, a novel and enhanced source for this biocatalyst would be useful to industry in the production of high value agrochemicals and pharmaceuticals.

SUMMARY OF THE INVENTION

The claimed invention is a process to produce 4-hydroxyproline comprising (a) contacting, in an aqueous reaction mixture, at least one starting material selected from the group consisting of trans-4-hydroxy-L-proline and cis-4-hydroxy-D-proline with an enzyme catalyst in a form selected from the group consisting of whole cells, cell extracts, partially purified enzyme or purified enzyme, the enzyme catalyst characterized by 4-hydroxyproline epimerase activity and derived from *Acinetobacter baumanni* WT-50/50-4A (ATCC 202144) or *Serratia marcescens* WT-L-4A1 (RED) (ATCC 202145); and (b) isolating the diastereomers trans-4-hydroxy-L-proline and cis-4-hydroxy-D-proline from the reaction mixture.

The invention encompasses biologically pure cultures of (a) *Acinetobacter baumanni* WT-50/50-4A designated as ATCC Accession Number 202144 and (b) *Serratia marcescens* WT-L-4A1 (RED) designated as ATCC Accession Number 202145.

Additionally, the invention includes a process to produce 4-hydroxyproline comprising (a) contacting, in an aqueous reaction mixture, at least one starting material selected from the group consisting of trans-4-hydroxy-D-proline and cis-4-hydroxy-L-proline, with an enzyme catalyst in a form selected from the group consisting of whole cells, cell extracts, partially purified enzyme and purified enzyme, the enzyme catalyst characterized by 4-hydroxyproline epimerase activity and derived from *Acinetobacter baumanni* WT-50/50-4A (ATCC 202144) or *Serratia marcescens* WT-L-4A1 (RED) (ATCC 202145); and (b) isolating trans-4-hydroxy-D-proline and cis-4-hydroxy-L-proline from the reaction mixture.

In both processes of the invention, the starting material can be recycled through steps (a) and (b) until it is ultimately converted to the corresponding diastereomer.

The processes are operated at a preferred pH of from about 6.0 to 8.0.

BRIEF DESCRIPTION OF THE BIOLOGICAL DEPOSITS

Applicants made the following biological deposits under the terms of the Budapest Treaty on the International Recognition of the Deposit of Microorganisms for the Purposes of Patent Procedure:

| Depositor Identification Reference | International Depository Designation | Date of Deposit |
| --- | --- | --- |
| Acinetobacter baumanni WT-50/50-4A | ATCC 202144 | 24 June 1998 |
| Serratia marcescens WT-L-4A1 (RED) | ATCC 202145 | 24 June 1998 |

As used herein, "ATCC" refers to the American Type Culture Collection international depository located at 10801 University Boulevard, Manassas, Va., 20110–2209, U.S.A. The "ATCC No." is the accession number to cultures on deposit with the ATCC.

DETAILED DESCRIPTION OF THE INVENTION

Applicants discovered 4-hydroxyproline epimerase activity in two isolated microorganisms, *Acinetobacter baumanni* WT-50/50-4A (ATCC 202144) and *Serratia marcescens* WT-L-4A1 (RED) (ATCC 202145). This epimerase activity usefully converts either trans-4-hydroxy-L-proline (THLP) or cis-4-hydroxy-D-proline (CHDP) to a mixture of CHDP and THLP.

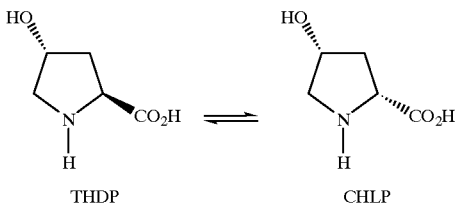

After conversion of THLP or CHDP to a mixture of THLP and CHDP, the two components of the product mixture are separated and the starting material recycled into the epimerization reaction mixture, whereby all of the starting material (THLP or CHDP) is ultimately converted to the corresponding diastereomer (CHDP or THLP, respectively).

The instant invention also relates to the use of 4-hydroxyproline epimerase activity in the two novel microorganisms, *Acinetobacter baumanni* WT-50/50-4A (ATCC 202144) and *Serratia marcescens* WT-L-4A1 (RED) (ATCC 202145), for the conversion of either trans-4-hydroxy-D-proline (THDP) or cis-4-hydroxy-L-proline (CHLP) to a mixture of CHLP and THDP.

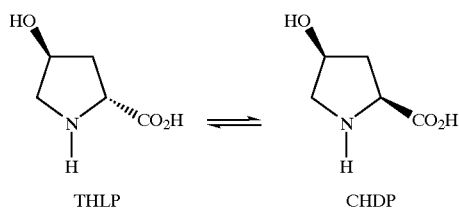

After conversion of THDP or CHLP to a mixture of THDP and CHLP, the two components of the product mixture are separated, and the starting material recycled into the epimerization reaction, whereby all of the starting material (THDP or CHLP) is ultimately converted to the corresponding diastereomer (CHLP or THDP, respectively).

Several advantages distinguish the method for enzymatically epimerizing 4-hydroxyprolines relative to chemical (non-enzymatic) methods of epimerization. First, the enzyme-catalyzed reactions run in the absence of the high concentrations of added acid or base required to chemically epimerize 4-hydroxyprolines. Second, the enzyme-catalyzed epimerization reaction can be performed at significantly lower temperatures preferably from about 5° C. to about 40° C. and lower pressures than those reported for chemical epimerization. In chemical epimerization, high reaction temperatures in the presence of strongly acidic or basic catalysts can result in yield loss. Relative to previously known chemical methods, the claimed invention generates little waste and permits a facile approach to product recovery.

The products of the present invention are useful as precursors for chemicals of high value in the agricultural and pharmaceutical industries.

In this disclosure, terms and abbreviations are defined as follows:

"Cis-4-hydroxy-D-proline" is abbreviated as CHDP.
"Cis-4-hydroxy-L-proline" is abbreviated as CHLP.
"Trans-4-hydroxy-L-proline" is abbreviated as THLP.
"Trans-4-hydroxy-D-proline" is abbreviated as THDP.
"High pressure liquid chromatography" is abbreviated as HPLC.
"Nuclear magnetic resonance" is abbreviated as NMR.

The term "diastereomer" describes stereoisomers not related as mirror images. Diastereomers are characterized by differences in physical properties and by some differences in chemical behavior towards achiral as well as chiral reagents.

"Enzyme catalyst" refers to a catalyst characterized by a 4-hydroxyproline epimerase activity. The catalyst may be in the form of whole microbial cell(s), permeabilized microbial cell(s), one or more cell component of a microbial cell extract, partially purified enzyme, or purified enzyme. The enzyme catalyst may also be immobilized using methods well-known to those of skill in the art.

DESCRIPTION OF THE PREFERRED EMBODIMENTS

Two novel microorganisms, *Acinetobacter baumanni* WT-50/50-4A (ATCC 202144) and *Serratia marcescens* WT-L-4A1 (RED) (ATCC 202145), both possessing 4-hydroxyproline epimerase activity, have been isolated for use in converting either trans-4-hydroxy-L-proline or cis-4-hydroxy-D-proline to a mixture of trans-4-hydroxy-L-proline (THLP) and cis-4-hydroxy-D-proline (CHDP). The 4-hydroxyproline epimerase activity of the two organisms is also useful for converting either trans-4-hydroxy-D-proline or cis-4-hydroxy-L-proline to a mixture of trans-4-hydroxy-D-proline (THDP) and cis-4-hydroxy-L-proline (CHLP).

Isolation of Single Microbial Cultures

The above strains were isolated from extracts of activated sludge collected at the Wilmington, Del., Wastewater Treatment Plant. Enrichment procedures were used with E2 Basal Medium (pH 7.2). E2 Basal Medium consists of the following chemicals in water:

| E2 Basal Medium | | | |
|---|---|---|---|
| | g/L | | g/L |
| $KH_2PO_4$ | 1.4 | $NiCl_2.6H_2O$ | 0.01 |
| $NaH_2PO_4$ | 0.6 | $CuCl_2.2H_2O$ | 0.005 |
| NaCl | 1.0 | biotin | 0.00002 |
| CaCl | 0.025 | folic acid | 0.00002 |
| KCl | 0.5 | pyridoxine HCl | 0.0001 |
| sodium citrate | 0.1 | riboflavin | 0.00005 |
| $MgSO_4.7H_2O$ | 0.5 | nicotinic acid | 0.00005 |
| $FeSO_4.7H_2O$ | 0.05 | pantothenic acid | 0.00005 |
| $CoCl_2.6H_2O$ | 0.01 | thiamine HCl | 0.00005 |
| $MnCl_2.4H_2O$ | 0.001 | vitamin $B_{12}$ | 0.000001 |
| $ZnCl_2$ | 0.0005 | p-aminobenzoic acid | 0.00005 |
| $NaMoO_4.2H_2O$ | 0.0025 | | |

The microbial sludge extract was cultured in shake flasks for 72 h at 30° C. in E2 medium containing 0.6% glycerol and a 1% trans-4-hydroxy-L-proline/cis-4-hydroxy-D-proline mixture having an L/D ratio of 60/40. The microbial harvest from the shake flask culture was streaked and passaged on agar plates containing E2 medium supplemented with 0.6% glycerol, 2.0% Bacto agar, and a 0.05%–1.0% trans-4-hydroxy-L-proline/cis-4-hydroxy-D-proline mixture having L/D ratios ranging between 60/40 and 20/80. Each isolate was grown in liquid culture using the same medium minus the agar to raise inoculum for 4-hydroxyproline epimerase screening studies. Over 100 microbial colonies were isolated and stored at −80° C. before testing for 4-hydroxyproline epimerase activity.

Epimerase Activity Screening of Isolated Microbial Cultures and Extracts

Each isolate was grown at 30° C. in unbaffled shake flasks containing 100 mL of E2 media for 24–48 h at 200 rpm. The cells were screened for 4-hydroxyproline epimerase activity in 1.0 mL reactions containing 50 mg/mL (wet cell weight) of cells or related extracts suspended in 50 mM phosphate buffer (pH 7.2) and 25 mg/mL CHDP. Cell extracts were prepared as needed by the addition of 1.0 mL of washed 0.5 mm glass beads (Biospec Products, Bartlesville, Okla.) to the reaction mixture, followed by vortexing in 10 sec pulses for a total of 2 min at 25° C. Following an 18 h incubation at 25° C. with mixing on a rotating platform, amino acid analysis for THLP/CHDP ratios in product mixtures was performed using either $^1$H NMR spectroscopy or HPLC. Two novel microbial strains which converted CHDP or THLP to a mixture of THLP/CHDP were isolated, identified and typed by fatty acid methyl ester (FAME) profile (AccuLab, Newark, Del.) as *Acinetobacter baumanni* WT-50/50-4A (ATCC 202144) and *Serratia marcescens* WT-L-4A1 (RED) (ATCC 202145).

The amount of 4-hydroxyproline epimerase activity in a reaction mixture is chosen to obtain the desired rate of reaction. The enzyme is added as whole cells, cell extract, partially purified enzyme, or purified enzyme. Concentrations of THLP or CHDP in reactions described by the present invention may vary and include concentrations up to and including their solubility limit in the reaction mixture. The solubility of THLP or CHDP depends on several parameters, including the temperature of the solution and the salt concentration (buffer) in the aqueous phase. Preferably, the pH of the reaction mixture is in the range of from 6.0 to 8.0 Initial concentration of THLP or CHDP preferably ranges from 50 mM to 500 mM, but higher concentrations may also be used. In cases of epimerizing THLP or CHDP with whole cells, the cells may be permeabilized by methods familiar to those skilled in the art (e.g., treatment with toluene, detergents, or freeze-thawing) to improve the rate of diffusion of hydroxyproline into and out of the cells.

THLP and CHDP mixtures produced by enzymatically epimerizing THLP or CHDP may readily be separated using the reported differences in chemical properties of the two compounds (e.g., solubility, solubility of copper salts, etc.; Greenstein, J. P. and Winitz, M., *Chemistry of the Amino Acids*, vol.3, chapter 29, John Wiley and Sons: New York (1961)). Other methods to separate compounds include, but are not limited to, ion exchange chromatography, electrodialysis, selective precipitation, or fractional crystallization. After separating the two components from the reaction mixture, the starting material can be recycled into the epimerization reaction, allowing the un-epimerized starting material (THLP or CHDP) to be converted to the corresponding diastereomer (CHDP or THLP, respectively).

EXAMPLES

The present invention is further defined in the following Examples. These Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

In the following examples, which serve to further illustrate the invention, analysis of mixtures of THLP or CHDP were performed by $^1$H NMR spectroscopy at 500 MHz, or by HPLC using a Beckman Model 6300 amino acid analyzer with post-column ninhydrin derivatization.

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

The meaning of abbreviations is as follows: "sec" means second(s), "min" means minute(s), "h" means hour(s), "d" means day(s), "$\mu$l" means microliter, "mL" means milliliters, "L" means liters, "mM" means millimolar, "M" means molar, "mmol" means millimole(s).

Example 1

Epimerization of THLP by Cell Extracts of *Acinetobacter baumanni* WT-50/50-4A or *Serratia marcescens* WT-L-4A1 (RED)

An aqueous solution containing THLP at a concentration of 191 mM, 95 mM or 63 mM in 50 mM potassium phosphate buffer (pH 7.0) was mixed with 50 mg (wet cell weight)/mL of *Acinetobacter baumanni* WT-50/50-4A (ATCC 202144) or *Serratia marcescens* WT-L-4A1 (RED) (ATCC 202145) at 25° C. Washed glass beads were added to this mixture and the resulting mixture vortexed in 10 sec pulses for a total of 2 min to disrupt the cells and produce a cell extract in situ. The resulting mixture was mixed on a rotating platform for 18 h at 25° C. Then the liquid portion of the mixture was separated from the glass beads, centrifuged, and the resulting supernatant analyzed for THLP and CHDP.

| cell extract | THLP initial concentration (mM) | % CHDP:% THLP (final) in reaction mixture |
| --- | --- | --- |
| A. baumanni WT-50/50-4A | 191 | 42:58 |
| A. baumanni WT-50/50-4A | 95 | 44:56 |
| A. baumanni WT-50/50-4A | 63 | 44:56 |
| S. marcescens WT-L-4A1 (RED) | 191 | 30:70 |
| S. marcescens WT-L-4A1 (RED) | 95 | 45:55 |
| S. marcescens WT-L-4A1 (RED) | 63 | 44:56 |

Example 2

Epimerization of CHDP by Cell Extracts of *Acinetobacter baumanni* WT-50/50-4A or *Serratia marcescens* WT-L-4A1 (RED)

An aqueous solution containing CHDP at a concentration of 191 mM, 95 mM or 63 mM in 50 mM potassium phosphate buffer (pH 7.0) was mixed with 50 mg (wet cell weight)/mL of *Acinetobacter baumanni* WT-50/50-4A (ATCC 202144) or *Serratia marcescens* WT-L-4A1 (RED) (ATCC 202145) at 25° C. Washed glass beads were added to this mixture and the resulting mixture vortexed in 10 sec pulses for a total of 2 min to disrupt the cells and produce a cell extract in situ. The resulting mixture was mixed on a rotating platform for 1 h at 25° C. Then the liquid portion of the mixture was separated from the glass beads, centrifuged, and the resulting supernatant analyzed for THLP and CHDP.

| cell extract | CHDP initial concentration (mM) | % CHDP:% THLP (final) in reaction mixture |
| --- | --- | --- |
| A. baumanni WT-50/50-4A | 191 | 41:59 |
| A. baumanni WT-50/50-4A | 95 | 44:56 |
| A. baumanni WT-50/50-4A | 63 | 44:56 |
| S. marcescens WT-L-4A1 (RED) | 191 | 61:39 |
| S. marcescens WT-L-4A1 (RED) | 95 | 45:55 |
| S. marcescens WT-L-4A1 (RED) | 63 | 44:56 |

Example 3

Epimerization of CHDP by Whole Cells of *Acinetobacter baumanni* WT-50/50-4A (ATCC 202144)

An aqueous solution containing 191 mM CHDP in 50 mM potassium phosphate buffer (pH 7.0) was mixed with 50 mg (wet cell weight)/mL of *Acinetobacter baumanni* WT-50/50-4A at 25° C. on a rotating platform for 18 h at 25° C. The resulting product mixture was centrifuged, and the resulting supernatant analyzed for THLP and CHDP.

| cells | CHDP initial concentration (mM) | % CHDP:% THLP (final) in reaction mixture |
| --- | --- | --- |
| A. baumanni WT-50/50-4A | 191 | 61:39 |

Example 4

Epimerization of THDP by Cell Extracts of *Acinetobacter baumanni* WT-50/50-4A or *Serratia marcescens* WT-L-4A1 (RED)

Using the methodology described in Example 1, an aqueous solution containing THDP at a concentration of 191 mM, 95 mM or 63 mM in 50 mM potassium phosphate buffer (pH 7.0) is mixed with 50 mg (wet cell weight)/mL of *Acinetobacter baumanni* WT-50/50-4A (ATCC 202144) or *Serratia marcescens* WT-L-4A1 (RED) (ATCC 202145) at 25° C. Washed glass beads are added to this mixture and the resulting mixture is vortexed in 10 sec pulses for a total of 2 min to disrupt the cells and produce a cell extract in situ. The resulting mixture is mixed on a rotating platform for 18 h at 25° C., then the liquid portion of the mixture is separated from the glass beads, centrifuged, and the resulting supernatant is analyzed for THDP and CHLP.

Example 5

Epimerization of CHLP by Cell Extracts of *Acinetobacter baumanni* WT-50/50-4A or *Serratia marcescens* WT-L-4A1 (RED)

Using the methodology described in Example 1, an aqueous solution containing CHLP at a concentration of 191 mM, 95 mM or 63 mM in 50 mM potassium phosphate buffer (pH 7.0) is mixed with 50 mg (wet cell weight)/mL of *Acinetobacter baumanni* WT-50/50-4A (ATCC 202144) or *Serratia marcescens* WT-L-4A1 (RED) (ATCC 202145) at 25° C. Washed glass beads are added to this mixture and the resulting mixture is vortexed in 10 sec pulses for a total of 2 min to disrupt the cells and produce a cell extract in situ. The resulting mixture is mixed on a rotating platform for 18 h at 25° C., then the liquid portion of the mixture is separated from the glass beads, centrifuged, and the resulting supernatant is analyzed for THDP and CHLP.

What is claimed is:

1. A process to produce diastereomers of 4-hydroxyproline comprising:
   (a) contacting, in an aqueous reaction mixture, at least one starting material selected from the group consisting of trans-4-hydroxy-L-proline and cis-4-hydroxy-D-proline with an enzyme catalyst in a form selected from the group consisting of whole cells, cell extracts, partially purified enzyme or purified enzyme, the enzyme catalyst characterized by 4-hydroxyproline epimerase activity and derived from *Acinetobacter baumanni* WT-50/50-4A (ATCC 202144) or *Serratia marcescens* WT-L-4A1 (RED) (ATCC 202145); and (b) isolating trans-4-hydroxy-L-proline and cis-4-hydroxy-D-proline from the reaction mixture.

2. A process to produce diastereomers of 4-hydroxyproline comprising:

(a) contacting, in an aqueous reaction mixture, at least one starting material selected from the group consisting of trans-4-hydroxy-D-proline and cis-4-hydroxy-L-proline, with an enzyme catalyst in a form selected from the group consisting of whole cells, cell extract, partially purified enzyme or purified enzyme, the enzyme catalyst characterized by 4-hydroxyproline epimerase activity and derived from *Acinetobacter baumanni* WT-50/50-4A (ATCC 202144) or *Serratia marcescens* WT-L-4A1 (RED) (ATCC 202145); and (b) isolating trans-4-hydroxy-D-proline and cis-4-hydroxy-L-proline from the reaction mixture.

3. The process of claim 1 or 2 wherein the reaction mixture has a pH of from about 6.0 to 8.0.

4. A biologically pure culture of *Acinetobacter baumanni* WT-50/50-4A designated as ATCC Accession Number 202144.

5. A biologically pure culture of *Serratia marcescens* WT-L-4A (RED) designated as ATCC Accession Number 202145.

6. The process of claims 1 or claim 2 further comprising (c) repeating steps (a) and (b) at least twice.

* * * * *